United States Patent [19]

Tycko

[11] Patent Number: 4,735,504
[45] Date of Patent: Apr. 5, 1988

[54] METHOD AND APPARATUS FOR DETERMINING THE VOLUME & INDEX OF REFRACTION OF PARTICLES

[75] Inventor: Daniel H. Tycko, Stony Brook, N.Y.
[73] Assignee: Technicon Instruments Corporation, Tarrytown, N.Y.
[21] Appl. No.: 547,513
[22] Filed: Oct. 31, 1983
[51] Int. Cl.⁴ ............................................. G01N 15/02
[52] U.S. Cl. .................................... 356/336; 356/343
[58] Field of Search ................. 356/39, 336, 338, 343

[56] References Cited

U.S. PATENT DOCUMENTS

| | | | |
|---|---|---|---|
| 3,705,771 | 12/1972 | Friedman et al. | 356/39 |
| 4,173,415 | 11/1979 | Wyatt | 356/336 |
| 4,273,443 | 6/1981 | Hogg | 356/343 |
| 4,492,752 | 1/1985 | Hoffman et al. | 356/39 |
| 4,548,500 | 10/1985 | Wyatt et al. | 356/336 |

FOREIGN PATENT DOCUMENTS

9307 4/1980 European Pat. Off. ............ 356/338

*Primary Examiner*—R. A. Rosenberger
*Attorney, Agent, or Firm*—Jeffrey M. Greenman

[57] ABSTRACT

A method and apparatus are disclosed for determining the volume and hemoglobin concentration of an isovolumetrically sphered red cell by passing the cell through a beam of monochromatic light to produce one forward light scattering pattern, and measuring the forward light-scattering pattern at two selected angular intervals to generate signals S1 and S2, respectively. The first angular interval is selected to span the angular region within which the first maxima of the light scattering patterns of the cells having volumes in the physiological range are expected to fall. The second angular interval is selected which begins above the upper limit of the first angular interval and below the second maximum of the scattering pattern of the cell having the largest volume in the physiological range and which extends to an angle at which the secondary maxima are reduced substantially to zero in comparison to the magnitude of the first maximum. The volume and index of refraction of the cell are then determined from the magnitude of the first and second signals S1, S2, by comparing the first and second signals, as a pair, to corresponding pairs of signals generated by cells of known volume and index of refraction. A method and apparatus for making such determination using a light beam of two wavelengths are also disclosed.

14 Claims, 6 Drawing Sheets

METHOD AND APPARATUS FOR DETERMINING THE VOLUME & INDEX OF REFRACTION OF PARTICLES

BACKGROUND OF THE INVENTION

1. Field of the Invention

The present invention relates to apparatus and method for determining diagnostically significant red blood cell parameters, i.e., hemoglobin concentration (HC) and volume (V), in a whole blood sample on a cell-by-cell basis by automated techniques. While finding particular application in the measurement of the HC and V of individual red blood cells, it will be appreciated that the present invention finds broad application in the measurement of the volume, or equivalently the diameter in the case of spherical particles, and index refraction index, or equivalently concentration of contents or density, of particles in general.

2. Description of the Prior Art

Variations in the morphological characteristics of red blood cells in a patient's blood sample provide valuable information concerning the pathological condition of many specific types of red cell disorders or anemias. Variations in size and color of individual red cells are highly correlated with their volume and hemoglobin concentration. In diagnosing such disorders, the mean cellular hemoglobin concentration (MCHC) and the mean cell volume (MCV) have also been measured to provide valuable insight into the condition of a patient. Such information is usually used in conjunction with the microscopic evaluation of the distribution of sizes, shapes and color of red cells in a stained blood smear by a trained hematologist and with other biochemical tests. For example, in mycrocytic anemias, the size of the red cells and, therefore, also the MCV are significantly reduced (microcytes) but the color and the MCHC are somewhat elevated. In megoblastic anemias, both the size (macrocytes) and the MCHC are somewhat increased.

Recent advances in cytology have produced numerous equipments for automatically measuring the characteristics of red cells, so as to cope with heavy laboratory workloads and with the spiraling increase in medical costs. The better known of such equipments, which are flow cytometers, are the TECHNICON H-6000 system (Technicon Instruments Corporation), the ORTHO ELT-8 system (Ortho Diagnostics) and the Coulter Model "S" system (Coulter Electronics, Dade, Fla.). All of these systems lyse a subsample of blood and measure the optical density of the solution to determine the whole blood hemoglobin concentration (HGB). Also, these systems provide methods for determining other red cell parameters but each based on a different measurement technique. In the TECHNICON H-6000 and the ORTHO ELT-8 systems, individual red cells are passed successively in suspension through a beam of light and the intensity of light scattered within a single angular interval by each such cell is detected and measured as a measure of cell size. The total number of such signals from a fixed volume of unlysed blood also provides the red blood cell count (RBC). The technique used in the TECHNICON H-6000 system for measuring the volume of a red blood cell relates cell volume to the intensity of light scattered by the cell. The intensity of the light scattered by a red blood cell is also dependent upon the refractive index of the cell which is almost entirely influenced by the concentration of hemoglobin in the cell. The hemoglobin and water account for about 99% of the cell contents. Thus, typically, the value of MCV of a sample of red blood cells which is calculated from a measurement of light scattered within a single angular interval depends also on the MCHC of the sample. In the Coulter Model "S" system, an electrical measurement is made whereby each cell is passed in turn through an orifice and the change in electrical resistance across such orifice is a measure of cell size. In the Coulter Model "S" system, a problem with MCHC interference is also present. The cells passing through the orifice are each subjected to significant hydraulic shear, so as to be deformed into an elongated and uniform shape. However, the amount of deformation of the cells is a function of the cell hemoglobin concentration, since it affects the cell viscosity. In a manner similar to that in the TECHNICON H-6000 system, the RBC is determined. Each of these systems accumulates the measurements which are then processed electronically for calculation of MCV which is proportional to the sum of the amplitudes of such measurements on individual cells divided by the number of cells measured. The packed cell volume (HCT) is calculated as the product of RBC and MCV; the MCHC is calculated by dividing HGB by HCT; and the mean cellular hemoglobin content (MCH) is calculated by dividing HGB by RBC. Each of these systems gives the mean measurement of the values of V and HC, that is, MCV and MCHC, respectively, and records the volumes of separate red cells as a distribution curve or histogram. However, such systems are incapable of determining HC on a cell-by-cell basis. Accordingly, an automated measurement of abnormal color variations on a cell-by-cell basis by flow cytometry has not been heretofore available to the diagnostician.

Techniques are known for simultaneously measuring the intensity of the light scattered in the forward direction and the intensity of the light absorbed by individual red blood cells in flow cytometry systems. The former measurement is used to estimate the volume of the cell and the latter measurement is used to estimate the hemoglobin content of the red blood cell. Such a sysem is described in the article "Combined Blood Cell Counting and Classification with Fluorochrome Stains and Flow Instrumentation" by H. M. Shapiro et al, Journal of Histochemistry and Cytochemistry, Vol. 24, No. 1, pp 396—411. An accurate measure of hemoglobin content can be determined by a light absorption measurement only if the index of refraction of the suspending medium matches the index of refraction of the red cells. Then the measurement will be free of an interfering pseudo-absorption scatter signal (see "The Photometric Chemical Analysis of Cells" by A. W. Pollister and L. Ornstein in *Analytical Cytology (R. Mellors, ed.)* p. 431, McGraw-Hill, New York, 1959). But then the red cells would not scatter light and the volume information would be lost. Therefore, in measurements such as those of Shapiro et al, where the indices of refraction have not been matched, each of the two measurements in fact depends upon both the volume and the index of refraction of the red blood cell being measured. Accordingly, this technique does not achieve an independent measurement of these cell parameters. Also, since the red blood cells being measured in such system are not sphered, the measurements obtained are not accurate.

Also, techniques are known for using image processing and pattern recognition technology to classify red blood cells. One such system is described in U.S. Pat. Nos. 3,851,156 and 4,199,748 and in the article "Image Processing for Automated Erythocyte Classification" by J. W. Bacus, the Journal of Histochemistry and Cytochemistry, Vol. 24, No. 1. pp. 195-201 (1976). In such a system, the sample is prepared as a monolayer of dried and flattened cells on a glass microscope slide and the images of individual red cells are analyzed by a microscope image processing and pattern recognition system, each cell being classified by appropriate logic circuits into a distinct subpopulation. Both the distributions of individual cell parameters as well as their means can be determined. However, the volume measurements are computed as being proportional to cell areas because cell thickness cannot be readily measured. However, since cell thickness in such preparations can vary, the above assumption is often in error. Such systems are also slower than flow cytometers, whereby fewer red blood cells per sample can be analyzed per unit time. Therefore, the results are somewhat degraded with respect to flow cytometers.

Further, additional techniques are known for measuring forward scattered light signals to determine the size of particles. For example, in "Particle Sizing by Means of the Forward Scattering Lobe" by J. Raymond Hodkinson, Applied Optics, Vol. 5, 1966, pp. 839-844 (also see P. F. Mullaney and P. N. Dean, Applied Optics, Vol. 8, p. 2361, 1969), the ratio of signals detected at two angles within the forward scattering lobe, or first maximum of the angular distribution of the scattered light, is measured to determine particle size. However, such techniques have been limited to the measurement of only a single parameter, i.e., size or volume, of the particles, and do not apply to the simultaneous measurement of size and index of refraction as do the methods to be described below.

SUMMARY OF THE INVENTION

In accordance with the present invention, light scattering techniques are employed to determine the index of refraction and the volume of particles which do not absorb the incident light or, in special cases, which are absorbing. The present invention provides that the index of refraction and volume of individual particles are simultaneously obtained.

The preferred practice of the invention is described with respect to sphered particles, e.g., isovolumetrically sphered red blood cells. However, the present invention is also applicable to the determination of the index of refraction and volume of particles slightly deformed from the spherical and also of non-spherical particles, but with corresponding loss of accuracy.

In the case of sphered red blood cells, such cells are entrained in a liquid medium or sheathed stream and passed successively through a light beam. The interception of the light beam by each cell produces a forward light scattering pattern about the light beam direction. The angular intensity distribution of such pattern is dependent upon fixed system parameters, i.e., wavelength of the light beam and index of refraction of the entraining liquid medium. Also, such intensity distribution is dependent upon the index of refraction, or equivalently, hemoglobin concentration HC, and the volume V of the red blood cell, which are the sole independent variable parameters of the system.

According to the present invention, the intensity of the light scattered by the red blood cell is measured at each of two selected angular intervals within the forward light scattering pattern. Again, such angular intervals, once determined, are fixed system parameters. In the case of a sphered red blood cell, the measurement of the intensity of the scattered light within the two angular intervals is determinative of the HC and V of the cell. Such angular intervals are selected such that the light intensities detected and measured within such angular intervals contain sufficient information for the precise independent determination of the HC and V of the red blood cell. Any variations in the light intensities within such angular intervals are a function only of the HC and V of the cell, i.e., the only independent system variables. As a result of measurement within the two angular intervals, a pair of signals S1 and S2 are generated, each of which is a function of both HC and V of the red blood cell. Accordingly, as particular values of HC and V generate distinctive S1 and S2 signals, the magnitudes of such signals is indicative of the HC and V of the cell. That is, particular magnitudes of S1 and S2 signals characteristic of a given red blood cell define a particular combination of HC and V values of such cell, such relationship following from the laws of scattering of electromagnetic radiation. The particular values of HC and V can be determined, for example, using a pre-computed table relating particular values of S1 and S2 to corresponding values of HC and V. Accordingly, the present invention relates to method and apparatus for simultaneously and accurately determining the volume and index of refraction of a particle, wherein:

a. the particle is caused to intercept a beam of light, so as to develop a forward light scattering pattern;

b. the light scattered within portions of such pattern is detected and measured to generate first and second signals;

c. the volume and index of refraction of such particle is determined from the magnitudes of such signals.

Preferably, the present invention is applicable to the measurement of properties of a spherical particle, wherein a monochromatic light beam is employed and the resulting light scattering pattern is measured at two angular intervals. However, the present invention can be practiced by employing a polychromatic light beam, wherein a plurality of forward light scattering patterns of two or more wavelengths is obtained. Again, selected portions of each of the forward light scattering patterns of different wavelengths are measured, to generate the equivalent S1 and S2 signals for determining the volume and index of refraction of the particle.

Also, the present invention finds application in the accurate measurement of the volume and index of refraction of non-spherical particles, preferably of a uniform shape and having an axis of rotational symmetry. In such event, the measurement of more than two angular intervals of the forward light scattering pattern is required as the number of independent variables within the system is increased. If all the uniformly shaped particles are similarly oriented (for example, by shear flow) when intercepting the light beam, the number of additional system parameters to be measured (e.g., angular intervals and/or wavelengths) would be reduced.

BRIEF DESCRIPTION OF THE DRAWINGS

For a more complete understanding of the present invention, reference should be made to the accompanying drawings, wherein.

DETAILED DESCRIPTION OF THE PREFERRED EMBODIMENT

Figure 1:
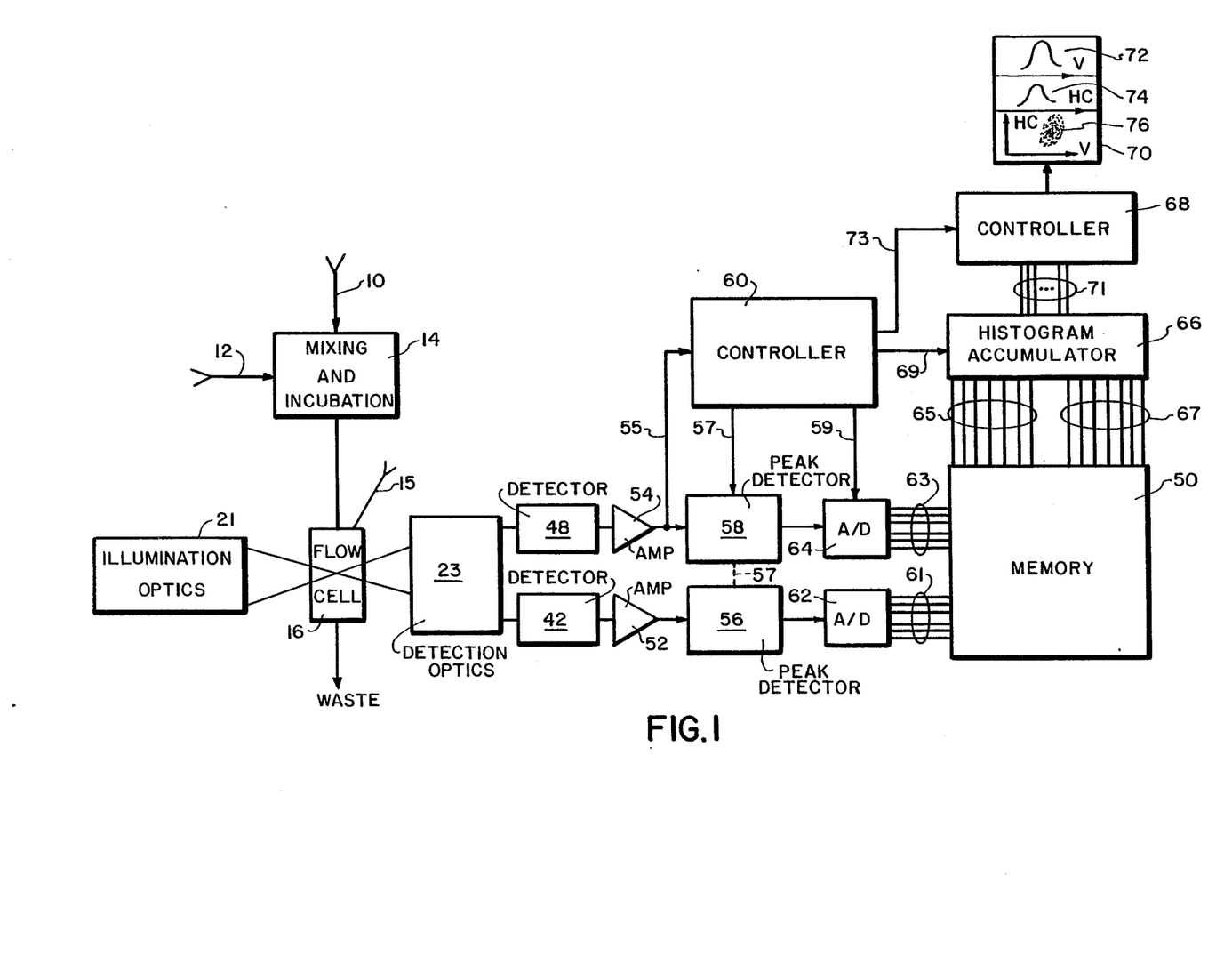
FIG. 1 is a block diagram of the preferred embodiment of the present invention.
Figure 2:
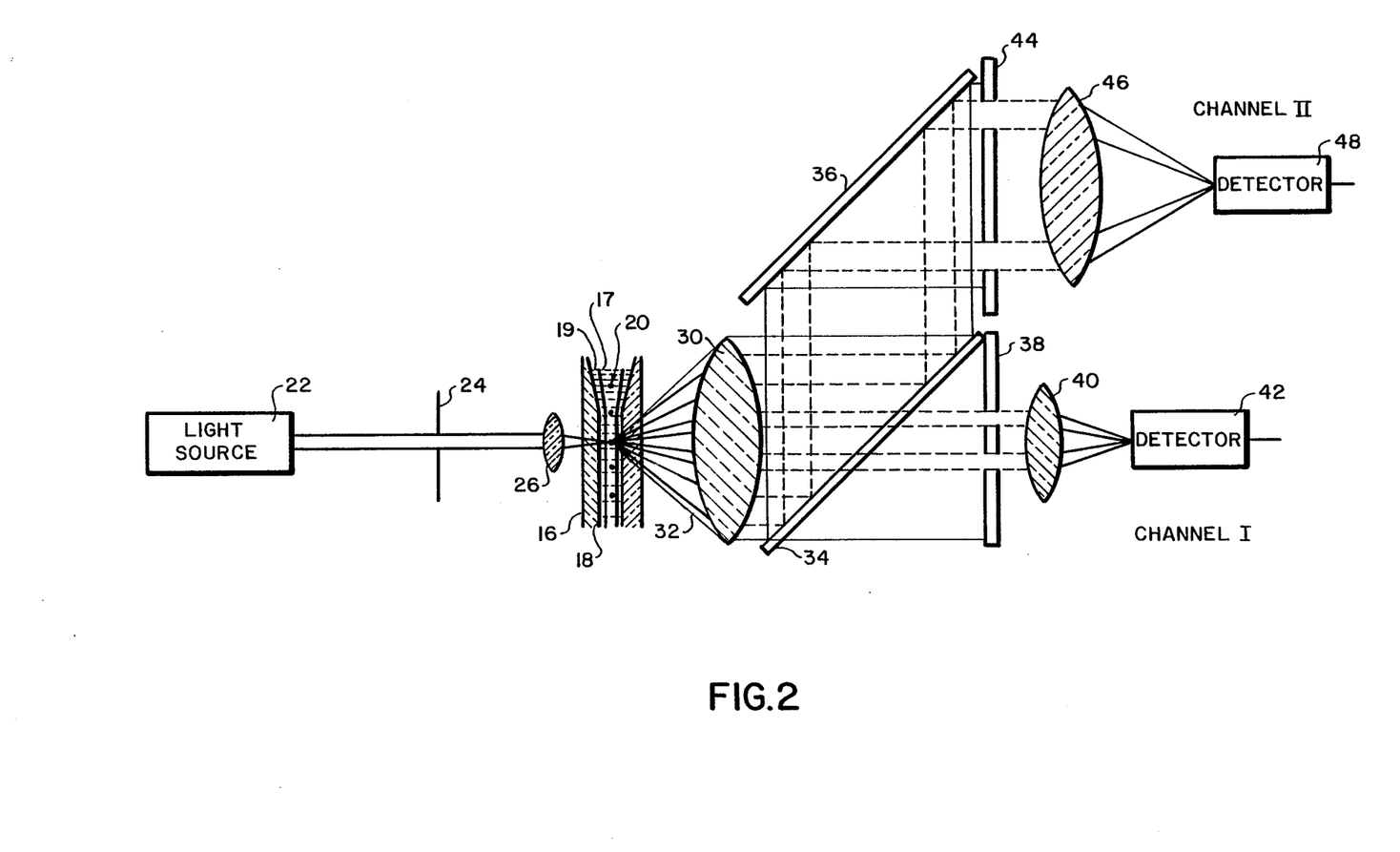
FIG. 2 is a schematic representation of the illumination and detection optics of FIG. 1.

Referring now to FIGS. 1 and 2 of the drawings, the system of the present invention comprises a conventional sampling apparatus, not shown, for introducing blood samples along a conduit 10. An isovolumetric sphering reagent is introduced along a second conduit 12. Such sphering reagent is, for example, described in the copending U.S. Ser. No. 277,539, assigned to a common assignee, and serves to sphere the red blood cells contained in the sample, without lysing such cells. Generally, mature non-nucleated red blood cells have a biconcave plate-like configuration, which would normally make the light-scattering signal dependent upon the orientation of the cell during optical measurement in a flow cytometer. To avoid such dependence, isovolumetric sphering of the red blood cell insures that measurement is completely independent of orientation of the cell.

The conduits 10 and 12 are directed to a mixing and incubation stage 14, whereat the individual cells are reacted with the sphering reagent. Normally, incubation is effected until the red cells have been sphered, as described in the above-identified copending U.S. Ser. No. 277,539. Following incubation, the sample now containing sphered red blood cells is passed through a sheath-stream flow cell 16 for measurement. Flow cell 16 can be of conventional design, for example, as described in U.S. Pat. No. 3,661,460, assigned to a common assignee, and operates such that the sample, or core, stream 17 is encased within a sheath stream 19 having an index of refraction the same as that of the sample stream 17. Sheath stream 19 is introduced to flow cell 16 along conduit 15. As the sample stream is passed through the flow cell, its diameter is progressively reduced, as shown in FIG. 2, by the narrowing of the internal diameter of the flow cell passageway 18.

The sample stream 17 is constricted to a dimension whereat the individual red blood cells 20 are caused to flow successively through an optically defined view volume, as is more particularly hereafter described. Each red blood cell 20, in turn, interrupts the light beam pasing through the view volume of flow cell 16 and causes light to be scattered in all directions in a pattern which is a function of the hemoglobin concentration HC and volume V of the red blood cell, as hereinafter further described.

FIG. 2 particularly illustrates the illumination optics 21 and detection optics 23 of FIG. 1 which are utilized to illuminate, in turn, each red blood cell 20 as it passes through flow cell 16 and to detect and measure the light scattered by such cell. As illustrated, the illumination optics comprises a light source 22, which may comprise a laser or a tungsten-halogen lamp. The illuminated field is defined by a precision slit aperture 24 which is imaged in the center of the sheathed sample stream 17 passing through flow cell 16 by an imaging lens 26. Alternatively, a laser illuminated field may be defined by an appropriate lens arrangement in lieu of the precision slit aperture 24.

As each sphered red blood cell passes, in turn, through the view volume of flow cell 16, it interrupts the light beam. Accordingly, light is scattered mainly in the forward direction and in an angular intensity pattern which, as defined by the laws of scattering of eletromagnetic radiation, is a function, inter alia, of the HC and V of the red blood cell. Such patterns are more particularly described with respect to FIGS. 3A–3C.

The detection optics include a lens 30 which collects the forward scattered light 32 and collimates the same, as illustrated. According to the invention, the forward scattered light within two critical angular intervals $\theta 1$ to $\theta 1 + \Delta\theta 1$ and $\theta 2$ to $\theta 2 + \Delta\theta 2$ (hereafter ($\theta 1$, $\Delta\theta 1$) and ($\theta 2$, $\Delta\theta 2$), respectively, are separately detected and measured to precisely determine the HC and V of each individual red blood cell. Accordingly, the light from lens 30 is directed to a beam splitter 34 which transmits approximately half the light and reflects the remaining light. The reflected light is directed to and reflected from a mirror 36.

Light scattered at the low angular interval ($\theta 1$, $\Delta\theta 1$) and at the high angular interval ($\theta 2$, $\Delta\theta 2$) is measured in channel I and channel II, respectively. As shown, light passed through the beam splitter 34 is directed along channel I through an annular opening in a dark field stop 38 adapted to pass light scattered within the low angular interval ($\theta 1$, $\Delta\theta 1$). Light passed by stop 38 is collected by lens 40 and focused onto a detector 42. Also, light reflected from mirror 36 is directed along channel II, which includes another annular opening in a dark field stop 44 adapted to pass light scattered within the high angular interval ($\theta 2$, $\Delta\theta 2$). Such light is collected by a second lens 46 and imaged onto a detector 48. Accordingly, the output of detector 42 is indicative of the amount of forward light scattered by a red blood cell within low angular interval ($\theta 1$, $\Delta\theta 1$) and the output of detector 48 is indicative of the amount of forward light scattered by a red blood cell within the high angular interval ($\theta 2$, $\Delta\theta 2$). As hereinafter described, such low and high angular intervals are selected such that light contained within these angular intervals contains sufficient information for the accurate and precise determination of the HC and V of the red blood cell being illuminated. Preferably, the transmission-reflection characteristics of beam splitter 34 is designed such that the intensities of the light incident upon detectors 42 and 48 are approximately equal, so as to maximize the signal-to-noise ratio of the system.

Figure 3A:
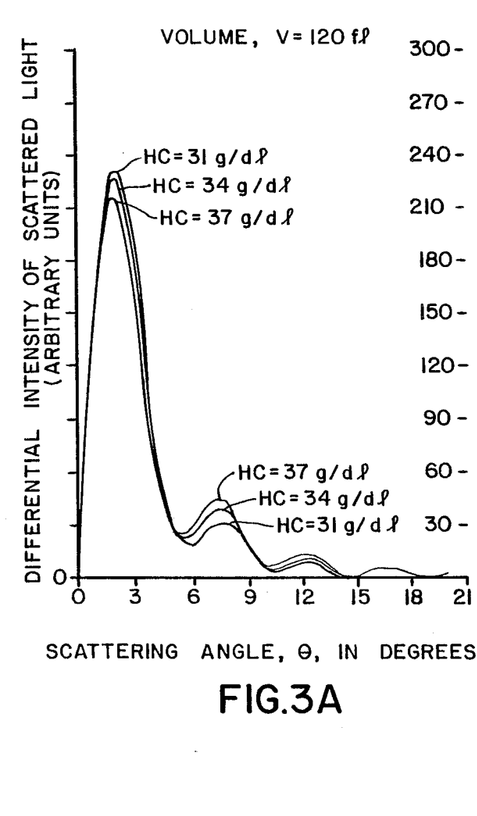
FIG. 3 illustrates a family of differential intensity patterns, or angular distributions, of light scattered in a forward direction by sphered red blood cells of the indicated parameters.
Figure 3B:
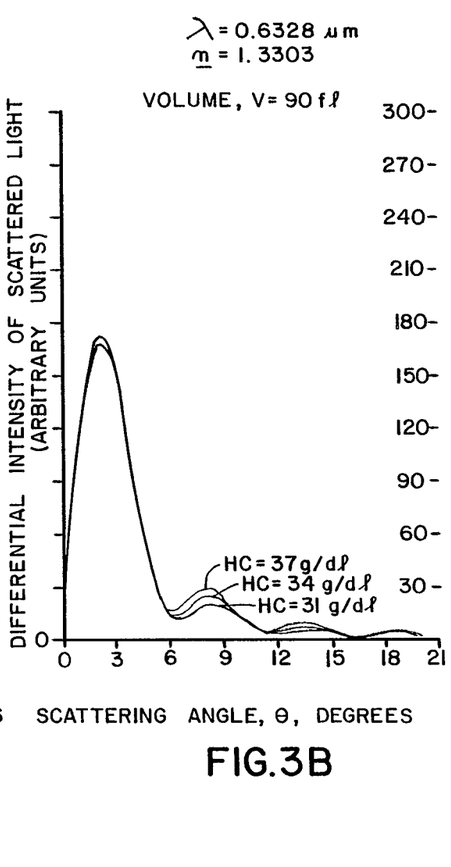
Figure 3C:
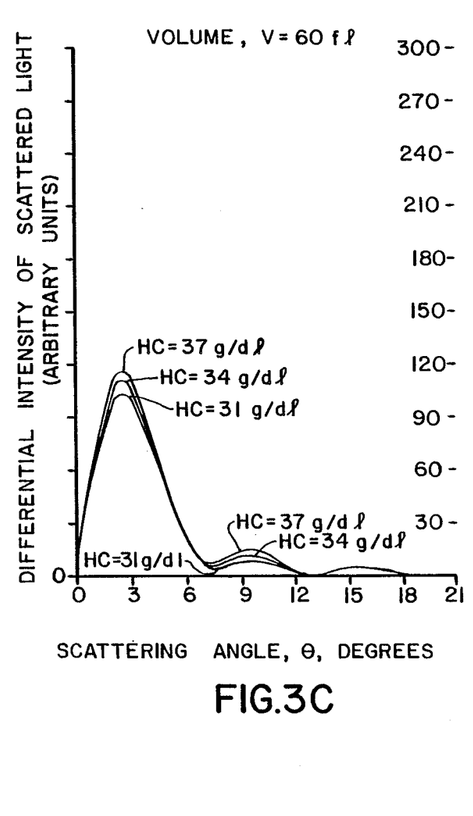

To more particularly understand the criticality of the low and high angular intervals ($\theta_1$, $\Delta\theta_1$) and ($\theta_2$, $\Delta\theta_2$), reference is made to FIGS. 3A–3C. The curves in FIGS. 3A–3C illustrate the so-called differential intensity patterns, of angular distributions, of light scattered by individual sphered red blood cells uniformly illuminated by a collimated light beam, of the indicated hemoglobin concentrations and volumes passing through the flow cell 16. As illustrated, the angular distributions have been multiplied by $\sin\theta$ and, therefore, are proportional to the light intensity scattered per unit scattering angle $\theta$. For a better understanding of these patterns, reference may be made to electromagnetic scattering theory for spherical particles (Mie theory), e.g., as described in *The Scattering of Light*, Milton Kerker, Academic Press (1969). The light scattered in the forward direction by a spherical particle (e.g., a non-nucleated, sphered red blood cell) has an angular distribution which is a function of the wavelength of the incident light ($\lambda$), the volume V (or equivalently the diameter) of the red blood cell, the hemoglobin concentration HC of the red blood cell (which determines its index of refraction) and the index of refraction of the medium in which the red blood cell is suspended, i.e. of the core stream 17. In the embodiment described, the index of refraction of the core stream 17 is determined solely by the physical properties of the sphering reagent (mainly water), to which the index of refraction of the sheath stream 19 is intentionally matched. The matched indices of refraction of the core and sheath streams 17 and 19 is hereafter referred to as n. Accordingly, the signal S generated by the detection of the forward scattered light can be represented mathematically by the equation $$S = f(\lambda, \theta, \Delta\theta, n, V, HC)$$

where ($\theta$, $\Delta\theta$) represents the angular interval within which such scattered light is detected. In a typical embodiment, the apparatus parameters $\lambda$, $\theta$, $\Delta\theta$ and n in such equation are fixed. If values of S with two different sets of apparatus parameters, e.g., two different angular intervals, were measured with respect to a same red blood cell, the resulting signals S1 and S2 would be generated, as represented by $$S1 = f(\lambda, \theta_1, \Delta\theta_1, n, V, HC) \quad (1)$$

$$S2 = f(\lambda, \theta_2, \Delta\theta_2, n, V, HC) \quad (2).$$

Accordingly, equations (1) and (2) have only two unknowns, i.e. HC and V. If the system parameters are chosen correctly, these two equations (1) and (2) can be solved for the two unknowns. If equations (1) and (2) were linear in HC and V, the values of the coefficients multiplying the two unknown variables would depend upon the values of the system parameters and such equations would have unique solutions if the value of the determinant of these coefficients was not zero. However, equations (1) and (2) are, in fact, not linear equations. In the case of non-linear equations, the so-called Jacobian determinant of equations (1) and (2) plays a role similar to the determinant of coefficients in the linear case. That is, the value of the Jacobian determinant, which depends upon HC, V, and the system parameters, must be non-zero if equations (1) and (2) are to yield single-valued solutions. (For example, reference is made to Chapter XII of Advanced Calculus by I. S. Sokolnikoff, McGraw-Hill, NY, 1939). The range of HC and V values for which the Jacobian determinant has non-zero values is dependent upon the values of the system parameters. Thus, the behavior of the Jacobian determinant can be used as a criterion when selecting the system parameters.

In general, equations (1) and (2) do not necessarily possess unique solutions for HC and V for all values of the angular parameters. This invention is based upon the discovery that a precise selection of the angular parameters ($\theta_1$, $\Delta\theta_1$) and ($\theta_2$, $\Delta\theta_2$) can be made, given the other fixed parameters of the system, i.e. $\lambda$ and n, such that equations (1) and (2) can be solved for unique values of HC and V over defined ranges. For red blood cells, such ranges would be typically 30 fl to 150 fl for V and 22 g/dl to 46 g/dl for HC which includes both the known normal and abnormal ranges for human red cells.

The respective magnitudes of the scattered light signals S1 and S2, represented by equations (1) and (2), respectively, are dependent upon HC because of the linear relationship of the index of refraction of the red blood cell ($n_C$) and the cellular hemoglobin concentration HC. Such linear relationship is expressed as $$n_C = A + (B \times HC) \quad (3)$$

In equation (3), the constant A is the index of refraction the red cell would have if HC were reduced to zero (approximately 1.33, the index of refraction of an isotonic aqueous solution at 0.6328 $\mu$m). Also, B is the specific refraction increment of hemoglobin (approximately 0.0019 dl/g if HC is measured in g/dl). (Reference is made to "Phase Contrast & Interference Microscopy in Cytology" by R. Barer in *Physical Techniques in Biological Research* (A. W. Pollister, ed.) Academic Press, 1966) Therefore, equations (1) and (2) can be replaced with equations in which $n_C$ appears instead of HC and the measurement technique of the invention would apply to the simultaneous measurement of the volume V and the index of refraction $n_C$ of any spherical dielectric particle.

In case the particles absorb as well as scatter light, the index of refraction $n_C$ is a complex number having a real part, $n_{CR}$, and an imaginary part, $n_{CI}$. For red blood cells, $n_{CR}$ is related to HC, as in equations (3), and $n_{CI}$ is related to HC through the equation $$n_{CI} = \frac{\ln 10}{4\pi} \lambda \epsilon_{mM} HC \quad (4)$$

where $\epsilon_{mM}$ is the molecular extinction coefficient of the hemoglobin at wavelength $\lambda$. Thus, $n_{CR}$ and $n_{CI}$ are not independent variables but are both dependent upon HC as in equations (3) and (4). Therefore, the form of equations (1) and (2) allow the determination of the volume and index of refraction of spherical dielectric particles, where such particles are either non-absorbing or, if absorbing, the real and imaginary parts of the index of refraction, $n_{CR}$ and $n_{CI}$, respectively, are related by a common factor.

To illustrate the selection of the low angular interval ($\theta_1$, $\Delta\theta_1$) and high angular interval ($\theta_2$, $\Delta\theta_2$), reference is made to FIGS. 3A–3C. FIGS. 3A–3C illustrate the intensities as a function of scattering angle, in arbitrary units, of light scattered in the forward direction by sphered red blood cells of 120 fl, 90 fl and 60 fl, respectively, passing in a sheath stream and through a light beam having a wavelength of 0.6328 μm. In FIGS. 3A-3C, the matched index of refraction n of the core and sheath streams is 1.3303. It will be appreciated that other wavelengths in the ultraviolet, visible or near infrared region of the spectrum can be used. Preferably, such wavelength is one, such as 0.6328 μm, which is only minimally absorbed by the red cell. Also, FIGS. 3A-3C illustrate the variations in the forward scattered intensity pattern due to variations in the index of refraction of the red blood cell, the latter being linearly related to the HC of such cell as per equation (3). FIGS. 3A-3C show the intensity patterns for HC values of 31 g/dl, 34 g/dl and 37 g/dl, as indicated. With respect to such patterns, it should be appreciated that the typical volume V of a normal red cell is 90 fl and the typical hemoglobin concentration HC of such cell is 34 g/dl. For red blood cells, the physiological range of V is between 60 fl and 120 fl and the physiological range of HC is between 31 g/dl. and 37 g/dl. The selections of ($\theta_1$, $\Delta\theta_1$) and ($\theta_2$, $\Delta\theta_2$) are made by considering the angular dependence of the scattering patterns over these ranges, as illustrated in FIGS. 3A-3C.

Figure 4:
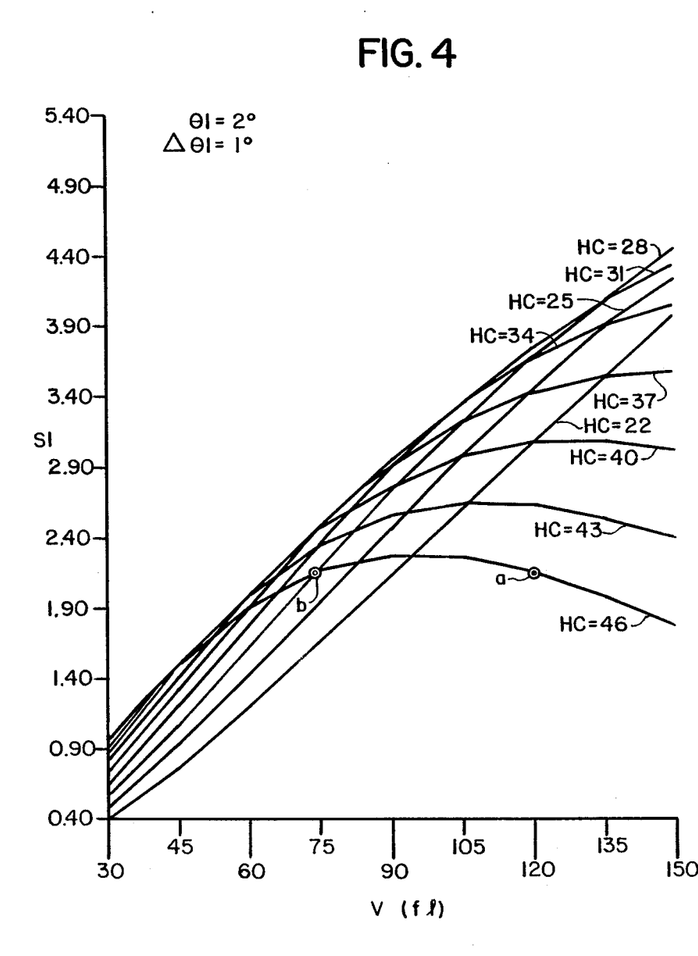
FIGS. 4 and 5 illustrate families of curves indicating the magnitudes of scattered light intensities measured within a first, or low, angular interval and a second, or high, angular interval, respectively, of the angular distributions illustrated in FIG. 3. Such magnitudes are plotted as a function of the hemoglobin concentration (HC) and volume (V) of sphered red blood cells, at the indicated system parameters.

The selection of the ($\theta_1$, $\Delta\theta_1$) is made to provide that the signal S1 varies significantly with variations of V. Referring to FIGS. 3A-3C, it is apparent that the first maximum is affected both by the HC and the V of the sphered red blood cell, the more significant variation being due to the latter. Accordingly, the ($\theta_1$, $\Delta\theta_1$) is selected to give an interval which is in the region (preferably spanning) the first maximum of each of the scattering patterns over the physiological range of V. As illustrated in FIG. 3B, the first maximum for the middle value of V, i.e., 90 fl, is $2\frac{1}{4}°$ off the optical axis. Also, the first maximum for the smallest value of V in the physiological range, i.e., 60 fl, is $2\frac{1}{2}°$ off the optical axis, as shown in FIG. 3C, and the first maximum of the largest value of V in the physiological range, i.e., 120 fl, is 2° off the optical axis, as shown in FIG. 3A. Accordingly, a satisfactory choice for ($\theta_1$, $\Delta\theta_1$) is from 2° to 3°, i.e., $\theta_1 = 2°$ and $\Delta\theta_1 = 1°$. The scattered light signal S1 detected within this angular interval varies as a function of both HC and V, yielding a S1 signal plotted against V and HC (where V varies between 30 fl and 150 fl and HC varies between 22 g/dl to 46 g/dl) as illustrated in FIG. 4. FIG. 4 shows that for a given value of S1, V is multivalued for certain values of HC. That is, for a given HC in the range 40 g/dl through 46 g/dl and for certain values of S1, V has two possible values. For example, for a value of S1 equal to 2.15 and for a HC of 46 g/dl, the red blood cell may have a volume V of 120 fl or 74 fl, as indicated by points a and b, respectively, in FIG. 4. This phenomenon is a manifestation of the fact which there can be many pairs of V and HC values which satisfy equation (1) for S1.

Figure 5:
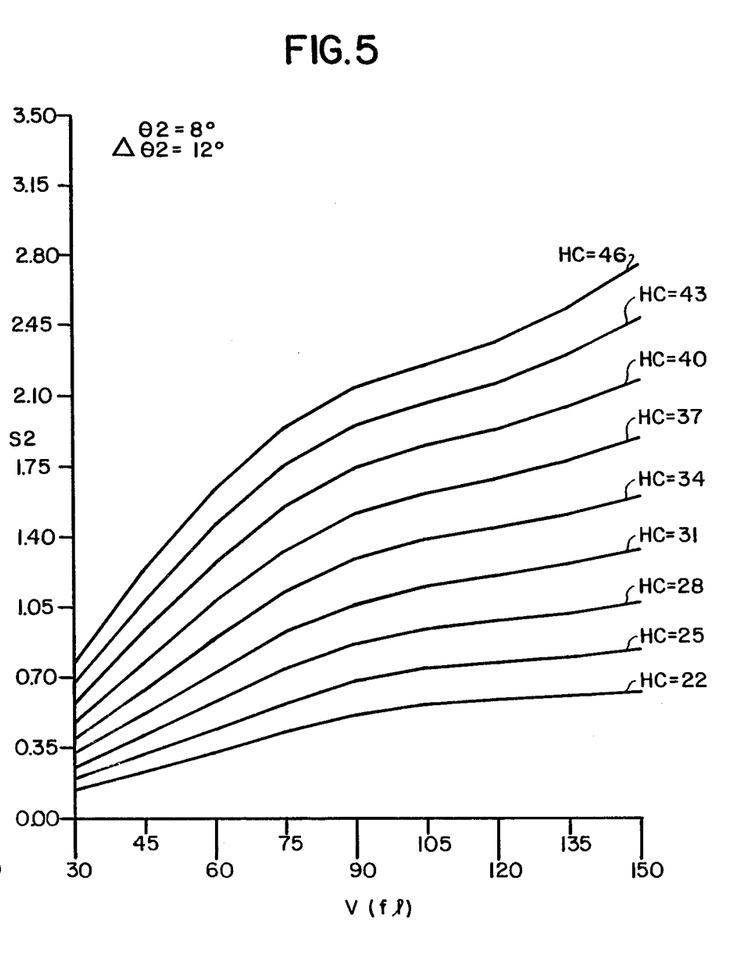

The high angle interval ($\theta_2$, $\Delta\theta_2$) is selected such as to resolve the ambiguities in the values of HC and V satisfying equation (1) for S1. Such resolution is achieved by selecting ($\theta_2$, $\Delta\theta_2$) to span a range of angles in the region above the first maximum of the scattering patterns obtained over the physiological ranges of HC and V. Such high angular interval ($\theta_2$, $\Delta\theta_2$) is selected, in the preferred embodiment, such that signal S2 varies monotonically with both HC and V over the range of interest. As illustrated in FIGS. 3A-3C, the secondary maxima of the scattering patterns increase in amplitude with both increasing HC and increasing V. However, the positions of these secondary maxima are very dependent on V and this positional variation will cause S2 to be non-monotonic unless ($\theta_2$, $\Delta\theta_2$) is wide enough to smooth or render ineffective the positional variability of such secondary maxima. Accordingly, the lower limit $\theta_2$ is preferably selected near the second maximum of the scattering pattern for the largest value of V in the physiological range, e.g. $\theta_2 = 8°$ in FIG. 3A. Also, the interval $\Delta\theta_2$ is preferably selected to be as large as possible consistent with practical optical considerations and signal-to-noise requirements of the system. The point whereat the scattering intensity in FIGS. 3A-3C reduce essentially to zero, e.g. at 20° serves well as an upper limit of the high angle interval, i.e., $\Delta\theta_2 = 12°$. Accordingly, the scattered light signal detected within the high angular interval ($\theta_2$, $\Delta\theta_2$) of 8° to 20° yields a plot S2 against HC and V (where V varies between 30 fl to 150 fl and HC varies between 22 g/dl to 46 g/dl) as illustrated in FIG. 5. If ($\theta_2$, $\Delta\theta_2$) are chosen correctly, the plot of S2 versus HC and V resolves the ambiguities discussed above. FIG. 5 shows that, with a high angular interval ($\theta_2$, $\Delta\theta_2$) of 8° and 20°, S2 varies monotonically with both HC and V. Consequently, as can be seen in FIG. 5, for any given value of S2, V is single valued for all values of HC. Therefore, any ambiguity present in equation (1), as discussed above, is resolved by equation (2).

In FIG. 2, the intensities of light scattered within ($\theta_1$, $\Delta\theta_1$) and ($\theta_2$, $\Delta\theta_2$) are measured concurrently with respect to a same angular intensity distribution pattern. However, it should be appreciated that such measurements can be made with respect to different angular intensity distribution patterns generated by a same red blood cell but separated in time and/or space, so as to obtain the S1 and S2 signals, respectively. By whatever manner the S1 and S2 signals are obtained, the HC and V of the red blood cell can be determined substantially simultaneously.

Figure 6:
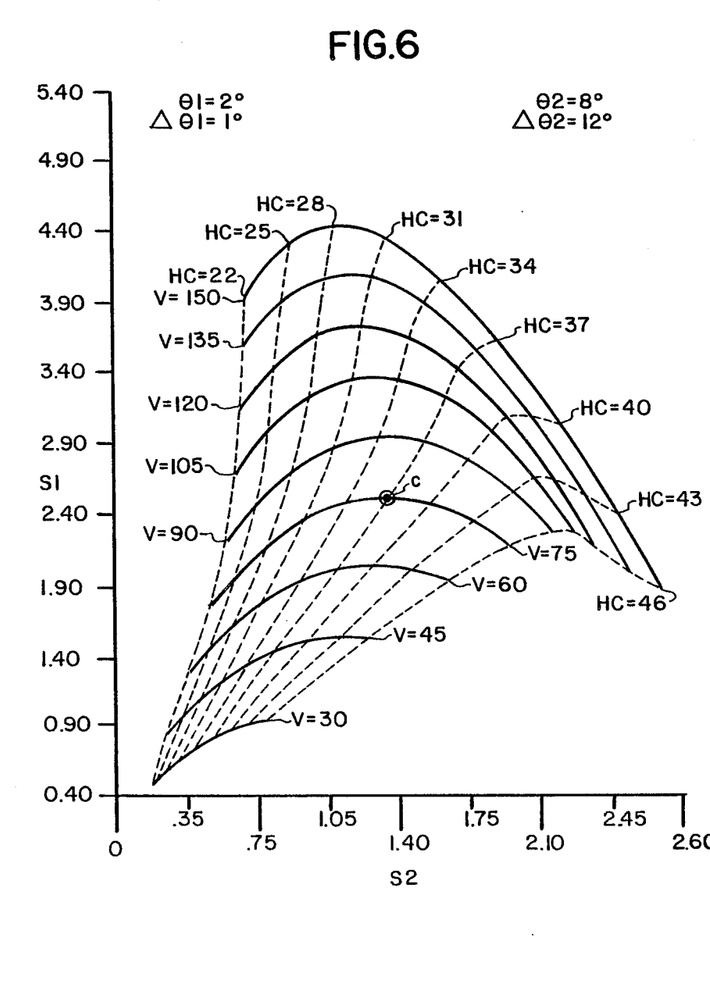
FIG. 6 illustrates a family of curves of the low and high angular measurements, as illustrated in FIGS. 4 and 5, respectively, plotted as a function of the and hemoglobin concentration (HC) and volume (V) of sphered red blood cells, at the indicated system parameters.

Accordingly, each sphered red blood cell intercepting the light beam from source 22 produces a pair of signals S1 and S2, whose respective magnitudes are functions of both the HC and V of such cell. Hence, the respective magnitudes of S1 and S2 are indicative of that HC-V pair which characterizes such cell. Each such pair of S1 and S2 signals can be plotted as a point in a S1-S2 plane, as illustrated in FIG. 6. If each point in the S1-S2 plane corresponds to a unique HC-V pair and also if two points in the S1-S2 plane, corresponding to the two HC-V pairs differing by the resolution requirements of the system, are separated by a practicably measurable amount, then the HC and V of the red blood cell can be determined with the required precision. In FIG. 6, the solid curves indicate variations of S1 and S2 as a function of HC for fixed values of V and the dashed curves indicate variations of S1 and S2 as a function of V for fixed values of HC. In such plot, since the constant-V curves are well separated and also the constant-HC curves are well separated, a single point in the S1-S2 plane represents a single HC-V pair, precisely identifying a single red blood cell with these characteristics. For example, in FIG. 6, point c represents a unique solution of equations (1) and (2) and represents a red blood cell having a V of 75 fl and an HC of 37 g/dl.

If ($\theta_1$, $\Delta\theta_1$) and ($\theta_2$, $\Delta\theta_2$) are not chosen as above described, the resulting S1-S2 plot may have indeterminate points, that is, single points which are indicative of more than one HC-V pair. Such condition would result, for example, when both S1 and S2 are not monotonic when plotted against HC and V over the desired dynamic ranges of HC and V. Hence, unique solutions of equations (1) and (2) for HC and V would not exist for all values of S1 and S2.

Figure 7:
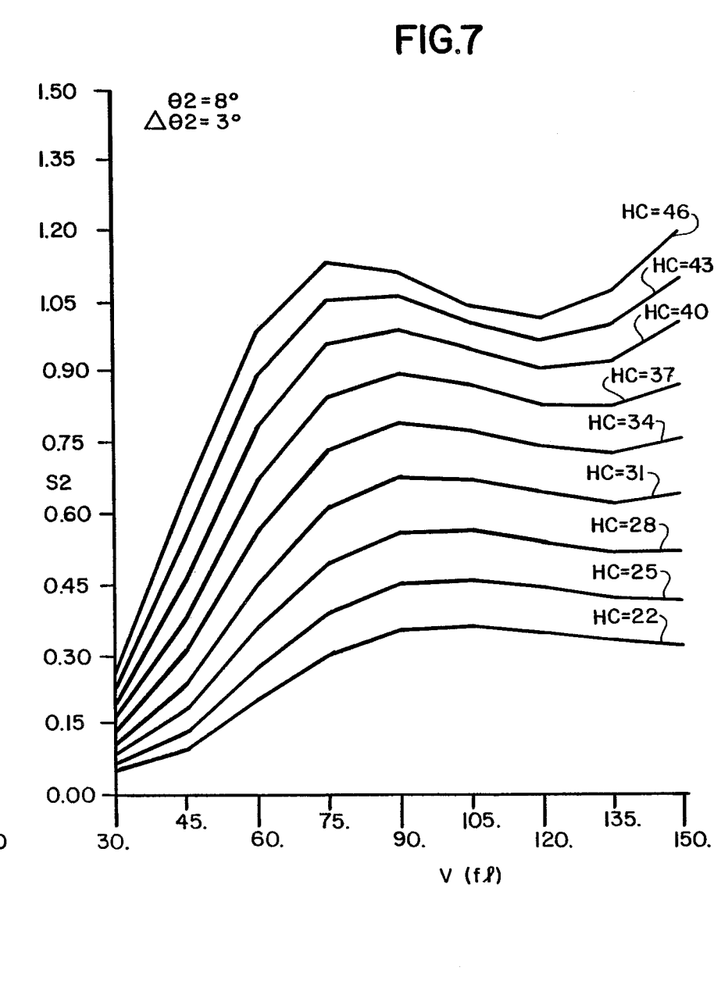
FIG. 7 illustrates a family of curves indicating the magnitudes of scattered light intensities measured within a high angular interval, as indicated, which is smaller than the high angular interval as represented by FIG. 5.
Figure 8:
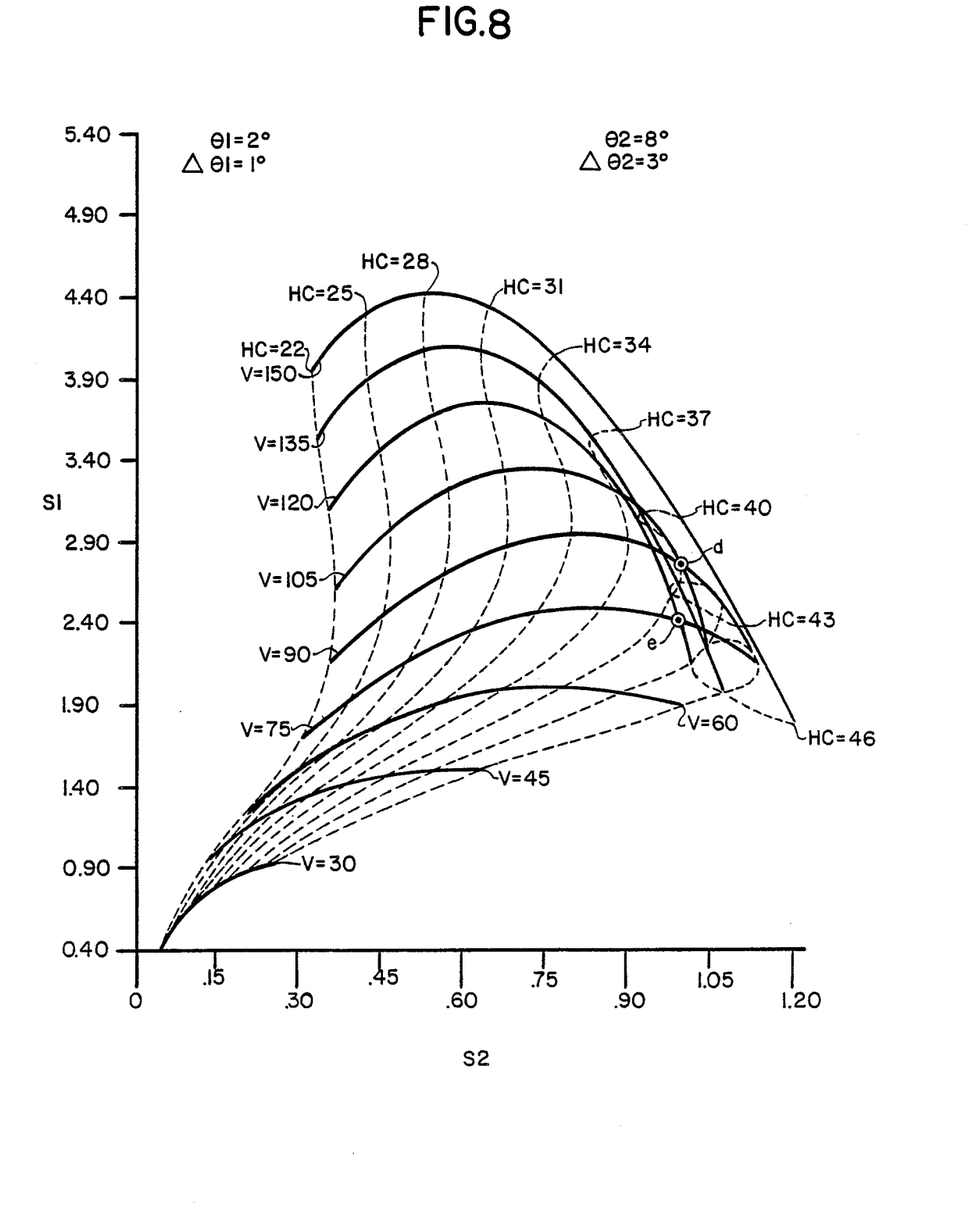
FIG. 8 illustrates a family of curves of the low and high angular measurements, as illustrated in FIGS. 4 and 7, respectively, plotted as a function of the hemoglobin concentration (HC) and volume (V) of sphered red blood cells, at the indicated system parameters.

This situation would, for example, result if $\Delta\theta 2$ were selected to be, say, 3° rather than 12° as discussed with respect to FIG. 5, i.e., the high angular interval is between 8° and 11° off the optical axis. In such event, signal S2 does not vary monotonically with HC and V over the range of interest. Such non-monotonic variation in the S2 plot is illustrated in FIG. 7 and results in a distortion of the of the S1-S2 plot, whereby that portion of the S1 and S2 plot representing higher values of HC and V folds over upon itself, as shown in FIG. 8. Accordingly, certain points in the S1-S2 plot of FIG. 8 representing these higher values of HC and V are no longer representative of single HC-V pairs, but rather represent a number of possible HC-V pairs. These ambiguous cases are illustrated by points d and e in FIG. 8. Point d is representative of a V value of 90 fl and an HC value of 40 g/dl and, also, a V value of 105 fl and HC value of 42 g/dl. Similarly, point e is representative of a V value of 75 fl and an HC value of 41 g/dl and also a V value of 120 fl and an HC value of 44 g/dl. Any point falling within the fold-over portion of the S1-S2 plot of FIG. 8 is indeterminant and would provide two or more possible solutions of equations (1) and (2). Obviously, such condition is not preferred. Notwithstanding, if a major portion of such a plot includes points which are single-valued, such condition may still be a useful one. In some cases, only one of the HC-V solution pairs would fall within the possible measurement ranges of HC or V and any other pairs could be discounted Accordingly, as equations (1) and (2) are solvable, numerical tables are employed which map S1-S2 pairs into unique HC-V pairs. Such tables are based upon the system parameters, i.e., $\theta 1$, $\Delta\theta 1$, $\theta 2$, $\Delta\theta 2$, n and $\lambda$. Such tables are stored as a look-up table in a decoding memory 50, as shown in FIG. 1, which is capable of receiving the S1 and S2 values and reporting the HC and V of each red blood cell. Such a table is precomputed using electromagnetic scattering theory and includes all resolvable HC-V pairs within the practical range of cell parameters to be measured. Alternatively, such HC-V pairs can be generated by real-time computation.

Referring again to FIG. 1, the outputs of detectors 42 and 48, which are proportional to the scattered light intensities within the low angular interval ($\theta 1$, $\Delta\theta 1$) and the high angular interval ($\theta 2$, $\Delta\theta 2$), respectively, are amplified by amplifiers 52 and 54, respectively. The nominal gains of amplifiers 52 and 54, i.e., G1 and G2, respectively, are adjustable to allow for calibration of the system. Also, amplifiers 52 and 54, preferably, include automatic gain control (AGC) to compensate for small variations which might occur in the intensity of the light beam. The respective outputs of amplifiers 52 and 54 are directed to peak detectors 56 and 58, respectively, which are of conventional design. Also, the output of amplifier 54 is applied along lead 55 to an input of a controller 60 which, upon receiving a signal from amplifier 54, applies a control pulse along lead 57 to peak detector 56 and 58. Peak detectors 56 and 58 track the output signals of amplifiers 52 and 54 and, then, store the peak value of such signals. The peak values stored in peak detectors 56 and 58, which are indicative of S1 and S2, respectively, are applied to the inputs of A/D converters 62 and 64, respectively. Alternatively, pulse integrating techniques can be used in lieu of peak detecting techniques to generate the S1 and S2 signals. Subsequently, controller 60 generates a convert pulse along lead 59, to enable the A/D converters 62 and 64 to each generate 6-bit signals along bus 61 and bus 63, indicative of the values of the S1 and S2 signals, respectively. Accordingly, the S1 and S2 signals, now digitized, are used to address memory 50 to retrieve the particular HC-V pair represented by the S1 and S2 signals. Concurrently, controller 60 applies a control pulse along lead 69 to activate a histogram accumulator 66.

The outputs of the memory 50, i.e., the HC and V values, are directed along two 7-bit buses, 65 and 67, respectively, to histogram accumulator 66 which counts the number of sphered red blood cells having the same values of HC and V within the range being measured. Histogram accumulator 66 comprises a memory of 16K words wherein each memory word corresponds to a particular pair of HC and V values and is incremented, i.e., an add-one operation is performed, whenever a measurement produces those values of HC and V. When a given number of red blood cells have been measured, controller 60 applies a control pulse along lead 73, directing a display controller 68 to read accumulator 66 along bus 71 and activate display 70 to produce displays of individual histograms 72 and 74 of V and HC, respectively, and also a two-dimensional frequency distribution 76 of HC-V pairs which characterize the red blood cells in the measured sample. It is a significant feature of the invention that the frequency distribution of V and HC of the individual red blood cells in the measured sample are displayed, as by histograms 72 and 74, respectively, along with the statistical correlation of HC and V contained in the two-dimensional frequency distribution 76, providing significant information to the diagnostician. Also, display 70 may have the capability to provide a paper print-out or hard copy of histograms 72 and 74 and also of the two-dimensional distribution 76. It should be evident that the histograms 72 and 74 and the two dimensional distribution 76 can be reported individually or in any combination.

The red blood cell indices MCV and MCHC are readily obtained from the volume histogram 72 and hemoglobin concentration histogram 74, respectively, by calculation of the mean values of the two histograms using standard statistical methods. Also, the widths of the two histograms, 72 and 74, are readily characterized by standard deviations and/or coefficients of variation, again using standard statistical methods. It should be appreciated that the present invention provides a means of quantitatively measuring the amount of red cell color variation in a sample of blood, something that heretofore has not been possible using flow cytometry techniques. For example, the standard deviation of the HC histogram 74 is such a measure since it measures the amount of cell-to-cell HC variation in the sample which, in turn, is responsible for the amount of cell-to-cell color variation in the sample. The coefficient of variation of the volume histogram 72 measures the so-called RDW index of the blood sample, a standard hematological parameter measured by instruments such as the TECHNICON H-6000 system and the Coulter Model "S" system.

It should be appreciated that the method described is applicable to the measurement of the volume and index of refractions of any spherical dielectric particle, which is either non-absorbing or absorbing as described above.

For example, a water-immiscible oil droplet passed through the flow cell could be measured for these parameters. If the index of refraction is known and is within the range, for example, encompassed by human red blood cells, such oil droplets can be used to calibrate the system. A suspension of such oil droplets, naturally sphered by surface tension forces, and having varying volumes within the range to be measured, are entrained in the sheath stream 19 and passed through the viewing volume of the flow cell 16. Each oil particle in turn, intercepts the light beam and produces a forward scattering pattern of the type illustrated in FIGS. 3A-3C. The forward scattered signals within the low angular interval $(\theta 1, \Delta\theta 1)$ and the high angular interval $(\theta 2, \Delta\theta 2)$ are measured to generate corresponding S1 and S2 signals, respectively. The S1 and S2 signals are passed through the system of FIG. 1, as described above, and the resulting HC histogram 74 is examined. Since all oil droplets have the same index of refraction, such a histogram consists of a very narrow peak. Preferably, oil droplets having several distinct indices of refraction, e.g., three, are employed to produce three distinct very narrow peaks in HC histogram 74. The proper calibration of the system is obtained by adjusting the gains G1 and G2 of amplifiers 52 and 54, respectively, to simultaneously minimize the widths of each of the three peaks. Accordingly, after calibration, pairs of S1 and S2 values produced by A/D converters 62 and 64, respectively, have the correct correspondence with HC-V pairs in the look-up table stored in memory 50. In effect, when the system is properly calibrated, the S1-S2 pairs obtained from oil droplet measurements would fall on a constant-HC curve corresponding to the refractive index of the oil when plotted on the grid of FIG. 6.

While it has been described that incident light of single wavelength $\lambda$ is used to generate the forward light scattering patterns illustrated in FIGS. 3A-3C, two distinct wavelengths $\lambda 1$ and $\lambda 2$ can be used by utilizing a polychromatic light source for source 22 in FIG. 2. In such event, each wavelength $\lambda 1$ and $\lambda 2$ generates distinctive scattering patterns, qualitatively similar to those illustrative in FIGS. 3A-3C, which vary as functions of HC and V of the scattering particle. Such patterns can be distinguished with respect to wavelength by proper optical techniques. For example, a dichoric mirror is substituted for beam splitter 34, such mirror having transmssion/reflection characteristics such that the scattering patterns of wavelengths $\lambda 1$ and $\lambda 2$ are directed to detectors 42 and 48, respectively, which are made selectively responsive to light of wavelengths $\lambda 1$ and $\lambda 2$, respectively. Accordingly, signals S1 and S2 are generated and directed to memory 50, as described above, which contains a precomputed table listing the corresponding HC-V pairs for each S1-S2 pair, whereby the appropriate histograms 72 and 74 of V and HC, respectively, and the two-dimensional frequency distribution 76 of the HC-V pairs are displayed.

In principle, the two wavelength technique described maintains all apparatus parameters fixed in equations (1) and (2), except for the variable parameters V and HC. In effect, equations (1) and (2) remain the same, except that $\lambda 1$ and $\lambda 2$ are substituted for $\lambda$ in equations (1) and (2), respectively. Again, the angular interval $(\theta 1, \Delta\theta 1)$ is selected such that signal S1 varies significantly with variations of V. Also, the angular interval $(\theta 2, \Delta\theta 2)$ is selected such as to resolve ambiguities in the values of HC and V in equation (1). $(\theta 1, \Delta\theta 1)$ and $(\theta 2, \Delta\theta 2)$ are selected as described above. Depending upon the range of the parameters of the particles being measured and also the relationship of wavelengths $\lambda 1$ and $\lambda 2$, it is conceivable that $(\theta 1, \Delta\theta 1)$ and $(\theta 2, \Delta\theta 2)$ may overlap in part or completely. For example, it is known that the forward light scattering pattern tends to become compressed in the direction of smaller scattering angles as the wavelengths of the light is increased. Accordingly, it is possible that the first maximum of the forward light scattering pattern of $\lambda 1$ may fall within the angular region of the secondary maxima in the forward light scattering pattern of $\lambda 2$. Therefore, by proper selection of $\lambda 1$ and $\lambda 2$, the angular intervals $(\theta 1, \Delta\theta 1)$ and $(\theta 2, \Delta\theta 2)$ may be overlapping or even equal. In the latter case, dark field stops 38 and 44 of FIG. 2 would be identical and adapted to pass the same angular interval of the scattered light patterns.

In principle, alternative embodiments of the present invention involve so-called extinction measurements for either or both S1 and S2 instead of the scattering measurements discussed above. When an extinction measurement is made of either S1 or S2, the corresponding angular interval, described above, would usually be defined by an annular aperture, rather than by an annular stop. Hence, the extinction, or reduction, of light passing through such aperture due to interception of the light beam by the particle would be approximately equal to that scattered into the angular interval discussed above.

For example, when S2 is a measure of light extinction within an angular interval between zero degrees and an angle near the second maximum of the scattering pattern (e.g., $\theta 2=0$, $\Delta\theta 2=8°$) and if the particle is weakly absorbing or non-absorbing at the wavelength $\lambda$, the measurement of S2 by an extinction method is essentially equivalent to measurement by the scattering method, as described above. For particles with appreciable absorption at wavelength $\lambda$, a further modification of the extinction method would make S2 an absorption measurement by using a small $\Delta\theta 2$ (e.g., approximately equal to the divergence angle of the illumination beam), such as in the system of H. M. Shapiro et al, discussed above. In this case, a careful choice of the system parameters can be made so that the appropriate equations (1) and (2) have single-valued solutions for HC and V within the required measurable range of these variables. Accordingly, such extinction-scatter and absorption-scatter methods are equivalent in principle to the scatter-scatter method, as described above, for accurately determining HC and V.

Also, the preferred embodiment has been described with respect to sphered red blood cells. However, the invention is applicable to the measurement of particles which are slightly deformed from the spherical and also non-spherical particles. In the case of the former, the measurements of HC and V would be less accurate than those for strictly spherical particles, the loss of accuracy depending upon the degree of deformation. In the case of the latter, which is an extreme case of the former, it may be that additional variables are introduced into the system. In such event, and depending upon the number of additional variables introduced, more than two angular intervals, which may or may not include $(\theta 1, \Delta\theta 1)$ and $(\theta 2, \Delta\theta 2)$, would be employed in the measurements.

For example, in the case of some properly oriented, uniformly shaped particles which have an axis of rotational symmetry, e.g., uniformly shaped spheroidal particles, the volume would be a function of the major and minor dimensions of such particle. To measure these particle parameters, flow cell 16 is structured to define a particular geometry of the core stream 17 such that the axis of rotational symmetry of the particles are all forced into a similar orientation with respect to the axis of the optical system. The index of refraction remains an independent variable. Accordingly, as the number of variables to be measured is increased to three, light scattered at three selected angular intervals would be measured to determine both the volume and index of refraction of the spheroidal particle.

What is claimed is:

1. A method for accurately determining the volume and index of refraction of an isovolumetrically sphered red blood cell comprising the steps of:
   a. passing said cell through a beam of light directed along an optical path to produce one forward light scattering pattern which is a function of the volume and index of refraction of said cell, said forward light scattering pattern representing scattered light intensity per unit scattering angle as a function of the scattering angle and which includes a first maximum and a plurality of secondary maxima;
   b. selecting a first angular interval which spans the angular region within which the first maxima of the light scattering patterns of cells having volumes in the physiological range are expected to fall;
   c. selecting a second angular interval which begins above the upper limit of the first angular interval and below the second maximum of the scattering pattern of the cell having the largest volume in the physiological range and extends to the angle at which the secondary maxima are reduced substantially to zero in comparison to the magnitude of the first maximum;
   d. generating, concurrently, first and second signals corresponding to the intensity of the scattered light within said first and second angular intervals respectively; and
   e. determining the volume and index of refraction of said cell from the magnitude of said first and second signals by comparing said first and second signals, as a pair, to corresponding pairs of signals generated by cells of known volume and index of refraction.

2. The method of claim 1 wherein said determining step includes the determination of the hemoglobin concentration of said red blood cell as a function of the index of refraction.

3. The method of claim 1, including the further steps of passing a plurality of particles having a uniform shape, in turn, through said beam of light, so as to generate signals corresponding to each of said particles, and determining the volume and index of refraction of each of said particles from the magnitudes of said corresponding corresponding signals.

4. The method of claim 1, including the further step of determining said second angular interval such that said second signal varies monotonically with the volume and index of refraction of each of said particle.

5. The method of claim 1, wherein said particles have a known index of refraction, and including the further step of scaling the magnitudes of said first and second signals produced by said particles of known index of refraction according to a precalculated relationship of volume and index of refraction, whereby the method is calibrated.

6. An apparatus for accurately determining the volume and index of refraction of an isovolumetrically sphered red blood cell comprising:
   a. means for directing a light beam along an optical path;
   b. means for passing said cell through said beam of light to produce one forward light scattering pattern which is a function of the volume and index of refraction of said cell, said forward light scattering pattern representing scattered light intensity per unit scattering angle and which includes first maximum and a plurality of secondary maxima;
   c. means for selecting a first angular interval which spans the angular region within which the first maxima of the light scattering patterns of the cells having volumes in the physiological range are expected to fall;
   d. means for selecting a second angular interval which begins above the upper limit of the first angular interval and below the second maximum of the scattering pattern of the cell having the largest volume in the physiological range and extends to the angle at which the secondary maxima are rendered substantially to zero in comparison to the magnitude of the first maximum;
   e. means for generating, concurrently, first and second signals corresponding to the intensity of the scattered light within said first and second angular intervals respectively; and
   f. means for determining the volume and index of refraction of said cell from the magnitude of said first and second signals by comparing said first and second signals, as a pair, to corresponding pairs of signals generated by cells of known volume and index of refraction.

7. The apparatus of claim 6 wherein said determining means determines the hemoglobin concentration of said red blood cell as a function of the index of refraction.

8. The apparatus of claim 6, further comprising means for passing a plurality of particles having a uniform shape, each in turn, through said beam of light, such that each of said particles develops, at least, one forward light scattering pattern, and wherein said generating means is operative to develop first and second signals corresponding to each of said particles, and said determining means is operative to determine the volume and index of refraction of each of said particles from the magnitudes of said corresponding first and second signals.

9. The apparatus of claim 8, wherein said passing means comprises a sheathed stream flow cell.

10. The apparatus of claim 8, wherein said determining means includes means for decoding said first and second signals into corresponding values of volume and index of refraction, and further comprising display means responsive to said decoding means for displaying at least, one of said corresponding values.

11. A method for accurately determining the volume and index of refraction of an isovolumetrically sphered red blood cell comprising the steps of:
   a. passing said cell through a beam of light of two wavelengths directed along an optical path to produce one forward light scattering pattern distinctive for each wavelength, each said forward light scattering pattern being a function of the volume and index of refraction of said cell and representing scattered light intensity per unit scattering angle as a function of the scattering angle and including a first maximum and a plurality of secondary maxima;

b. selecting for the light of the longer wavelength, an angular interval which spans the angular region within which the first maxima of the light scattering patterns of cells having volumes in the physiological range are expected to fall;

c. generating first and second signals corresponding to the intensity of the scattered light within said angular interval for each of said two wavelengths respectively; and d. determining the volume and index of refraction of said cell from the magnitude of said first and second signals by comparing said first and second signals, as a pair, to corresponding pairs of signals generated by cells of known volume and index of refraction.

12. The method of claim 11 wherein said determining step includes the determination of the hemoglobin concentration of said red blood cells as a function of the index of refraction.

13. An apparatus for accurately determining the volume and index of refraction of an isovolumetrically sphered red blood cell comprising:

a. means for directing a beam of light of two wavelengths along an optical path;

b. means for passing said cell through said beam of light to produce one forward light scattering pattern distinctive for each wavelength, each being a function of the volume and index of refraction of said cell and representing scattered light intensity per unit scattering angle and including first maximum and a plurality of secondary maxima;

c. means for selecting for the light of the longer wavelength an angular interval which spans the angular region within which the first maxima of the light scattering patterns of the cells having volumes in the physiological range are expected to fall;

d. means for generating first and second signals corresponding to the intensity of the scattered light within said angular interval for each of said two wavelengths respectively; and e. means for determining the volume and index of refraction of said cell from the magnitude of said first and second signals by comparing said first and second signals, as a pair, to corresponding pair of signals generated by cells of known volume and index of refraction.

14. The apparatus of claim 13 wherein said determining means determines the hemoglobin concentration of said red blood cell as a function of the index of refraction.

* * * * *